April 30, 1968 E. S. BOERNER Plant Pat. 2,809
ROSE PLANT
Filed Jan. 11, 1967
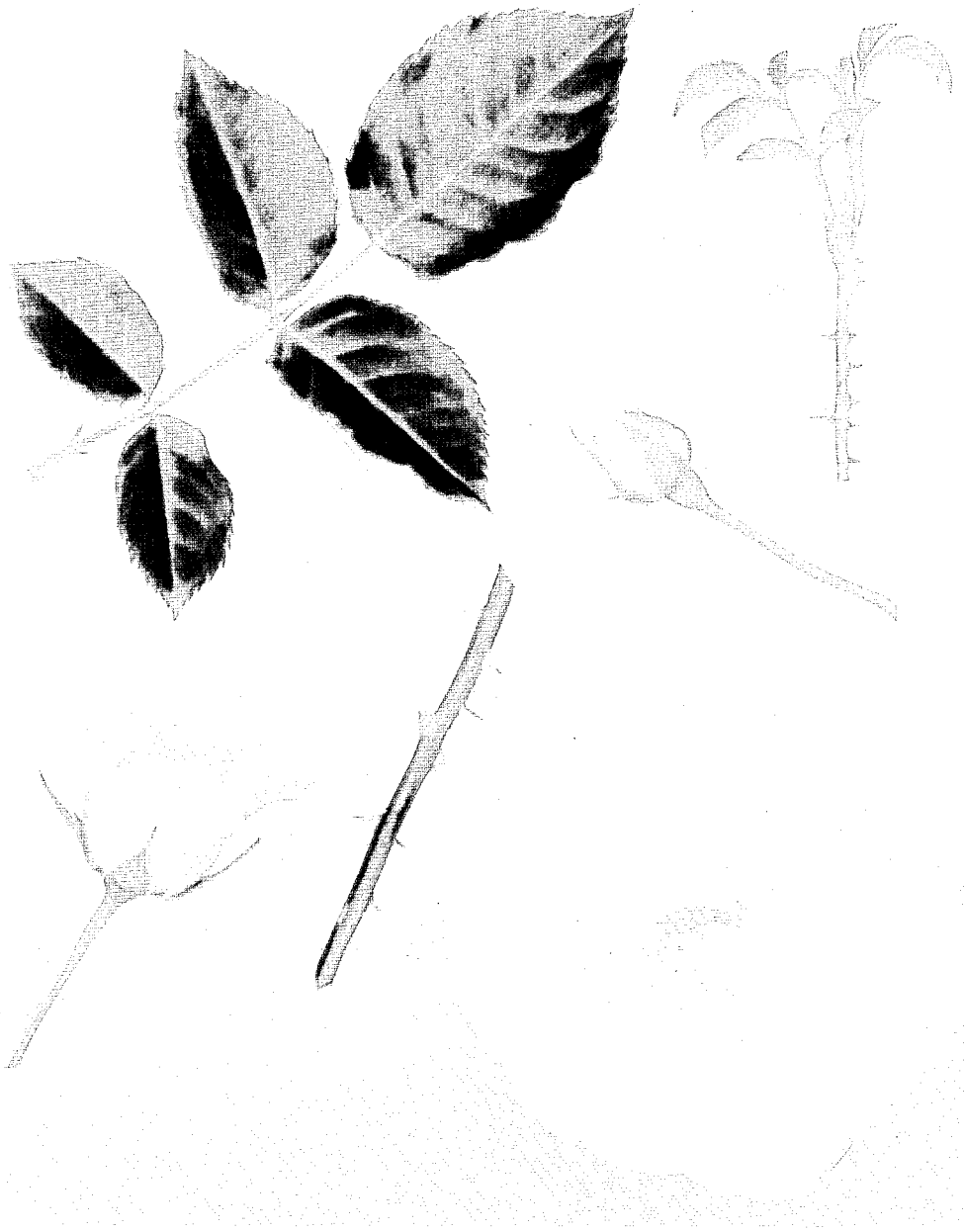
Inventor.
E. S. Boerner, Deceased
By: Lincoln Rochester Trust Company
By: Edward L. Jenner, Asst. Trust Officer
and Roger L. Boerner
Executors.
By: Robb & Robb
Attorneys.

United States Patent Office

Plant Pat. 2,809
Patented Apr. 30, 1968

2,809
ROSE PLANT

Eugene S. Boerner, deceased, late of Benton, N.Y., by Lincoln Rochester Trust Company, Rochester, N.Y., and Roger L. Boerner, Milwaukee, Wis., executors, assignors to Jackson & Perkins Company, Newark, N.Y., a corporation of New York Filed Jan. 11, 1967, Ser. No. 608,708
1 Claim. (Cl. Plt.—24)

The present invention relates to a new and distinct variety of rose plant of the fluoribunda class, which was originated by the late Eugene S. Boerner, deceased, by crossing the rose variety known as "Golden Garnette" (Plant Patent No. 1,898) with an unnamed and unpatented climbing seedling of the variety known as "Yellow Pinocchio" (Plant Patent No. 992).

The primary objective of this breeding was to produce a new and improved rose variety which bears longer stemmed flowers than those of the variety "Golden Garnette," while retaining the fragrance and flower color of "Golden Garnette." This objective was fully achieved, along with other desirable features, as evidenced by the following unique combination of characteristics which are outstanding in the new variety and which distinguish it from its parents, as well as from all other varieties:

(1) A flower productivity equal to that of "Golden Garnette," but with the flowers borne on longer cutting stems;

(2) A larger flower size than the flowers of "Golden Garnette," with more petals per flower; and (3) A flower color and fragrance similar to "Golden Garnette."

Asexual reproduction of the new variety by budding, as performed at Newark, N.Y., and also at Pleasanton, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature:

Parentage: Seedling.
*Seed parent.*—"Golden Garnette."
*Pollen parent.*—An unnamed climbing seedling of "Yellow Pinocchio."

Classification:
*Botanic.*—Floribunda.
*Commercial.*—Floribunda.

*Flower*

(Observations made from specimens grown in a greenhouse at Newark, N.Y., in the early morning near the middle of the month of July.)

Blooming habit: Recurrent—continuous.

Bud:
*Size.*—Large.
*Form.*—Ovoid; is not affected by wet or hot weather.
*Color.*—When sepals first divide—Deep Chrome, Plate 3. When petals begin to unfurl—Light Orange-Yellow, Plate 3. When half-blown: inside of petals—Apricot Yellow, Plate 4, lighting overcast with Maize Yellow, Plate 4; reverse of petals—Light Cadmium, Plate 4, with upper half of petal overcast with Maize Yellow, Plate 4.
*Sepals.*—Slightly branched; curl back when petals begin to unfurl. Color: inside—Rainette Green, Plate 31; outside—Chromium Green, Plate 32.
*Calyx.*—Color—Chromium Green, Plate 32. Shape—funnel. Size—small. Aspect—smooth. Odor when rubbed—none.
*Peduncle.* — Length — medium. Aspect — rough. Strength — erect; slender. Color — Cosse Green, Plate 5.
*Opening.*—Opens up well; is not affected by adverse weather conditions.

Bloom:
*Size.*—Large. Average size when fully expanded—from 3½ inches to 4½ inches.
*Borne.*—Both singly and several together.
*Stems.*—Long; strong.
*Form (when first open).*—Full. Permanence—retains its form to the end, but outer petals curl back.
*Petalage.*—Double (full but open center). Number of petals under normal conditions—from 35 to 40.
*Color.*—Center of flower—Empire Yellow, Plate 4. Outer petals—Baryta Yellow, Plate 4, with lower half of petal overcast with Pinard Yellow, Plate 4. Base of petals (aiglet)—Martius Yellow, Plate 4. Inside of petals—Empire Yellow, Plate 4, with outer edge of petal lightly overcast with Maize Yellow, Plate 4. Reverse of petals—Baryta Yellow, Plate 4, lightly overcast with Maize Yellow, Plate 4. General tonality from a distance—Empire Yellow, Plate 4, with outer edge of petal lightly overcast with Maize Yellow, Plate 4.
*Discoloration.*—General tonality at end of first day—Empire Yellow, Plate 4, lightly overcast with Maize Yellow, Plate 4 in upper half of petal. Second day—Empire Yellow, Plate 4, lightly overcast with Maize Yellow, Plate 4 in upper half of petal. Third day—Empire Yellow, Plate 4, overcast lightly with Baryta Yellow, Plate 4.

Petals:
*Texture.*—Thick; is not affected by wet or hot weather.
*Appearance.*—Inside—satiny. Outside—shiny.
*Form.*—Oval; slightly notched.
*Arrangement.* — Imbricated (regularly arranged shingle-like).
*Petaloids in center.*—Few; small.
*Persistence.*—Drop off cleanly.
*Fragrance.*—Strong. Nature—fruity (russet apple).
*Lasting quality.*—On the plant—very long. As cut flower—very long.

*Genital organs*

Stamens, anthers: Medium size; many; regulary arranged around styles. Color—Light Ochraceous-Buff, Plate 15.
Stamens, filaments (threads): Short. Color—Sulphur Yellow, Plate 5.
Pollen: Color—Pale Ochraceous-Buff, Plate 15.
Styles: Columnar; uneven length; medium length; thin.
Stigmas: Color—Maize Yellow, Plate 4.
Ovaries: All enclosed in calyx.
Hips: None.
Seeds: None.

*Plant*

Form: Bush.
Growth: Vigorous; upright; branching.
Foliage: Compound of 5 to 7 leaflets.
*Size.*—Large.
*Quantity.*—Normal.
*Color.*—New foliage: upper side—Yellowish-Citrine, Plate 16, with serrations Burnt Sienna, Plate 2; under side—Rainette Green, Plate 31, very lightly overcast with Vinaceous-Rufous, Plate 14. Old foliage: upper side—Forest Green, Plate 17; under side—Light Elm Green, Plate 17.

*Shape.*—Oval pointed.

*Texture.*—Upper side — leathery and glossy. Under side—smooth.

*Ribs and veins.*—Ordinary.

*Edge.*—Serrated (saw toothed).

*Serration.*—Both double and single; small.

*Leaf stem.* — Color — Ecru-Olive, Plate 30. Under side—smooth.

*Stipules.*—Medium length; smooth.

Wood:

*New wood.*—Color—Olive Lake, Plate 16. Bark—smooth.

*Old wood.*—Color—Forest Green, Plate 17. Bark—smooth.

Thorns:

*Thorns.*—Quantity: on main stalks from base—ordinary; on laterals from stalk — ordinary. Form — narrow base; medium length; some hooked downward and some hooked upward. Color (when young)—Tawney-Olive, Plate 29. Position—irregular.

*Prickles.* — Quantity: on main stalks — none; on laterals—none.

*Short needles.*—Quantity: on main stalks—none; on laterals—none.

What is claimed is:

1. A new and distinct variety of rose plant of the floribunda class, substantially as herein shown and described, characterized particularly as to novelty by the unique combination of a flower productivity equal to that of "Golden Garnette," but with the flowers borne on longer cutting stems, a larger flower size than the flowers of "Golden Garnette," with more petals per flower, and a flower color and fragrance similar to "Golden Garnette."

No references cited.

ROBERT E. BAGWILL, *Primary Examiner.*